United States Patent [19]

Priarone et al.

[11] 4,319,842
[45] Mar. 16, 1982

[54] PHOTOMULTIPLIER PROTECTOR FOR A FLUOROMETER

[75] Inventors: Paolo Priarone, Hyattsville; Peter A. St. John, Adelphi, both of Md.

[73] Assignee: Baxter Travenol Laboratories, Inc., Deerfield, Ill.

[21] Appl. No.: 169,607

[22] Filed: Jul. 17, 1980

[51] Int. Cl.³ ............................................. G01N 21/64
[52] U.S. Cl. .................................... 356/317; 250/458; 356/244
[58] Field of Search ............... 356/311, 317, 318, 244, 356/417; 250/458, 461 R, 461 B, 361 C; 422/52

[56] References Cited

U.S. PATENT DOCUMENTS 4,213,703 7/1980 Haunold et al. ................. 250/361 C
4,291,230 9/1981 Heiss .................................... 250/458

Primary Examiner—F. L. Evans
Attorney, Agent, or Firm—Robert A. Benziger; Thomas R. Vigil; Paul C. Flattery

[57] ABSTRACT

The photometer is adapted for sensing radiation emitted by a chemical sample held in a cuvette received in a first compartment and includes a highly sensitive photomultiplier in a second compartment adjacent the first compartment for detecting fluorescent radiation emitted by the chemical sample and passing through an opening between the compartments. A mechanical protector assembly is provided for protecting the photomultiplier from ambient light and includes a movable light shield movable between a first position blocking the opening and a second position not blocking the opening. A knob is provided for moving the light shield to the first position to protect the photomultiplier from light entering from the first compartment when the first compartment is opened for insertion or removal of a cuvette, and for moving the light shield to the second position not blocking the opening to permit radiation emitted by the chemical sample to impinge upon the photomultiplier in the second compartment. The photometer also includes a mechanical interlocking assembly for ensuring that the first compartment cannot be opened unless the light shield is in the first position to prevent ambient light from entering the second compartment from the first compartment and reaching the photomultiplier.

3 Claims, 7 Drawing Figures

PHOTOMULTIPLIER PROTECTOR FOR A FLUOROMETER

BACKGROUND OF THE INVENTION

1. Field of the Invention

The present invention relates to a photometer in which fluorescent radiation is detected by a very sensitive photomultiplier. More specifically, the present invention relates to an assembly which prevents ambient light from striking the photomultiplier tube when a compartment for receiving a sample-containing cuvette is open but which allows fluorescent light emitted by the chemical sample to strike the photomultiplier tube when the compartment is closed.

2. Description of the Prior Art

Heretofore, difficulties have been encountered in protecting from ambient light a very sensitive photomultiplier for detecting weak fluorescent light emitted by a sample being irradiated by a light source. One method of preventing damage to the photomultiplier tube is to electrically turn off the circuit to the photomultiplier tube before a first compartment for receiving a sample-containing cuvette is opened. This method has the disadvantage that the gain of the photomultiplier tube may shift when the voltage to the photomultiplier tube is turned off and turned on again. To alleviate, if not altogether obviate this problem, the present invention provides an assembly with interlocking parts which permit the weak fluorescent light to illuminate the photomultiplier tube when the first compartment is closed and which shields the photomultiplier tube from strong ambient room light when the first compartment is opened.

As will be described in greater detail hereinafter, the present invention provides a very simple and inexpensive mechanical assembly for protecting a sensitive photomultiplier tube used to detect fluorescent radiation in a photometer from incident room light.

SUMMARY OF THE INVENTION

According to the invention there is provided in a photometer which is particularly adapted for sensing radiation emitted by a chemical sample held in a cuvette in a first compartment and which includes a highly sensitive photomultiplier in a second compartment adjacent the first compartment for detecting fluorescent radiation emitted by the chemical sample and passing through an opening between the compartments, the improvement comprising: means for protecting the photomultiplier from ambient light, said protecting means including a movable light shield movable between a first position blocking the opening and a second position not blocking the opening and means for moving said light shield to said first position to protect said photomultiplier from light entering from the first compartment when the first compartment is opened for insertion or removal of a cuvette, and for moving said light shield to said second position not blocking the opening to permit radiation emitted by said chemical sample to impinge upon the photomultiplier in the second compartment.

DESCRIPTION OF THE PREFERRED EMBODIMENT

Figure 1:
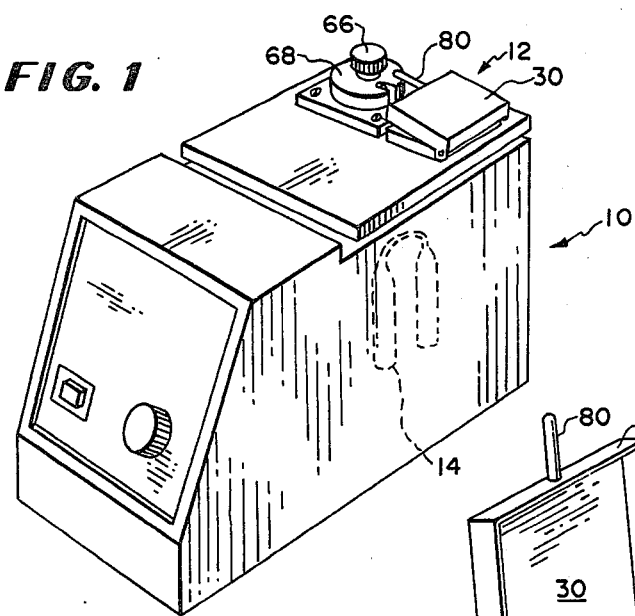
FIG. 1 is a perspective view of the photometer of the present invention viewing the same from a front upper corner thereof.
Figure 7:
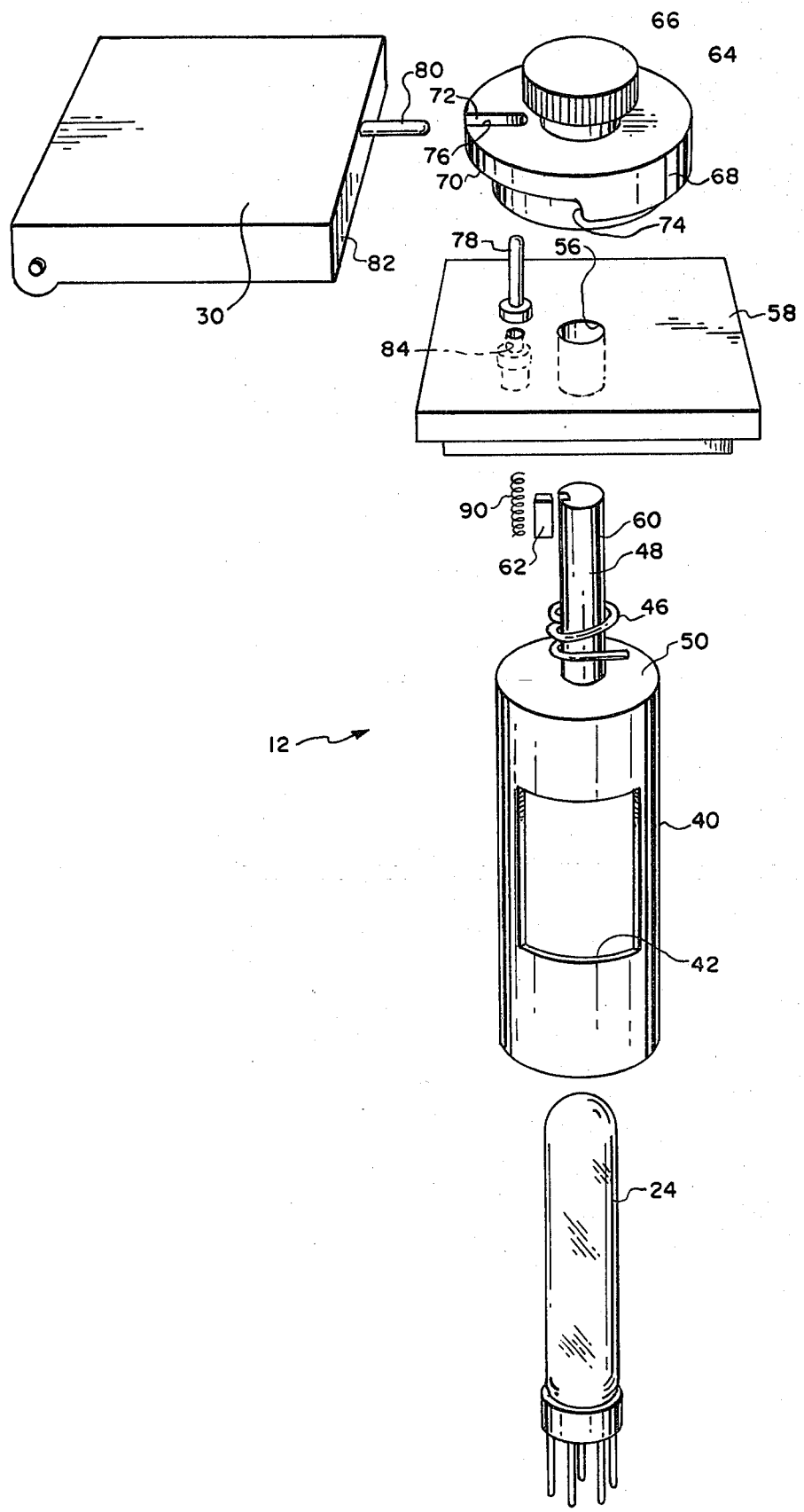
FIG. 7 is an exploded perspective view of the photomultiplier protector assembly of the present invention.

Referring now to the drawings in greater detail, there is illustrated in FIG. 1 a photometer 10 including a photomultiplier protector assembly 12 made in accordance with the teachings of the present invention. The photomultiplier protector assembly 12 is best illustrated in FIG. 7 and will be described in further detail hereinafter.

Figure 2:
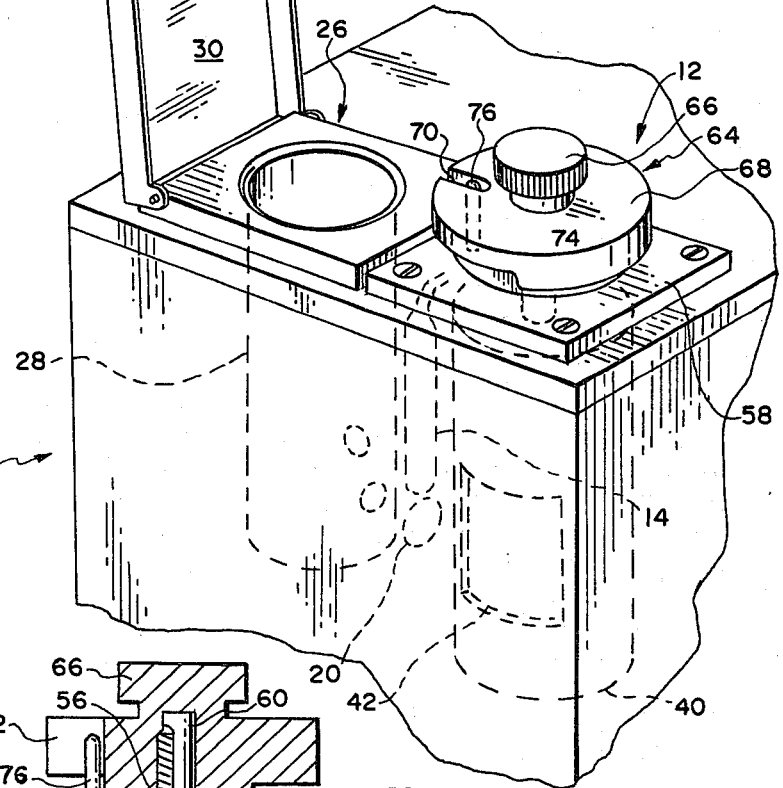
FIG. 2 is a fragmentary perspective view of the back upper corner of the photometer shown in FIG. 1 with a cuvette-receivng chamber, a light source and photomultiplier-protecting light shield shown in phantom.
Figure 3:
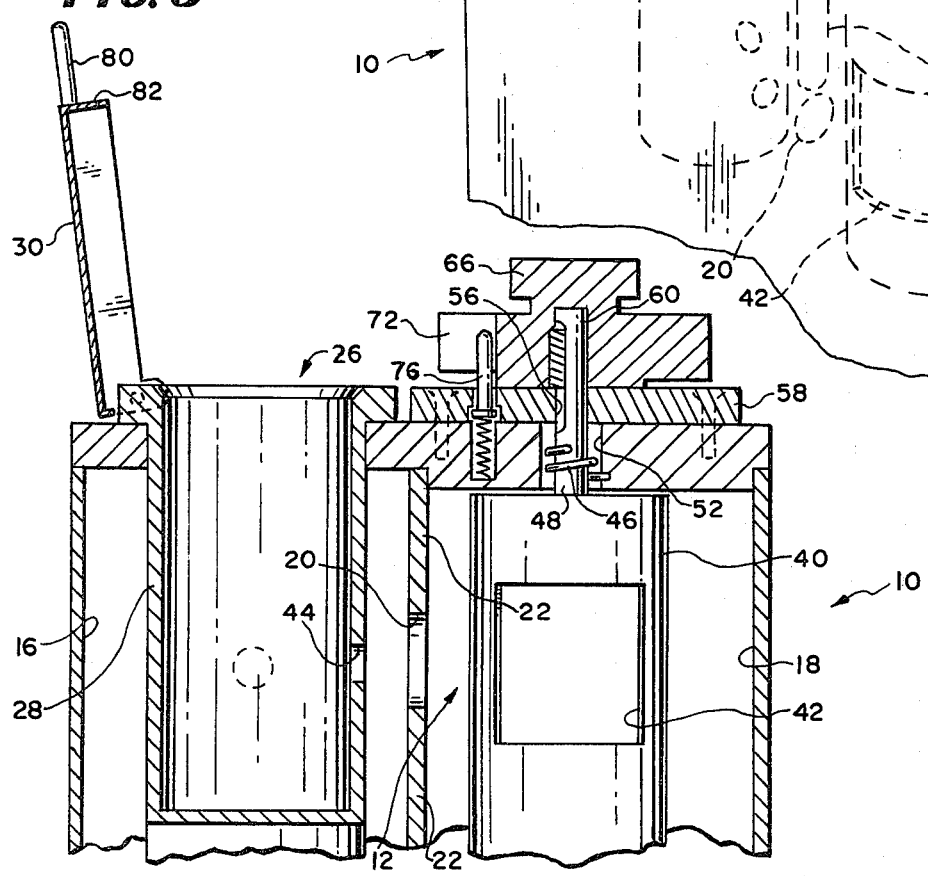
FIG. 3 is a vertical sectional view showing a cover for the cuvette-receiving chamber in a raised, open position.
Figure 4:
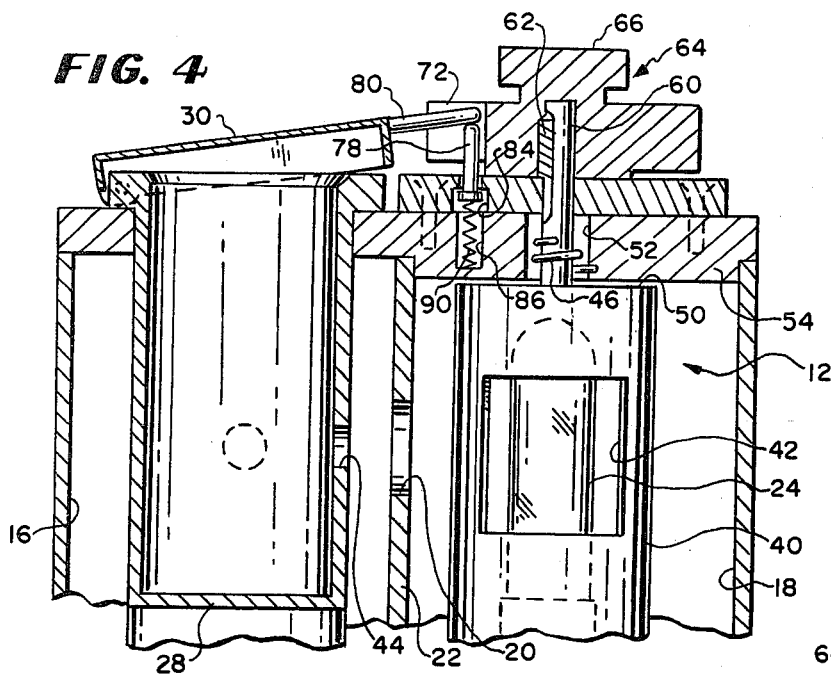
FIG. 4 is a vertical sectional view similar to FIG. 3 showing the cover for the cuvette-receiving chamber in a lowered, partially closed position.
Figure 5:
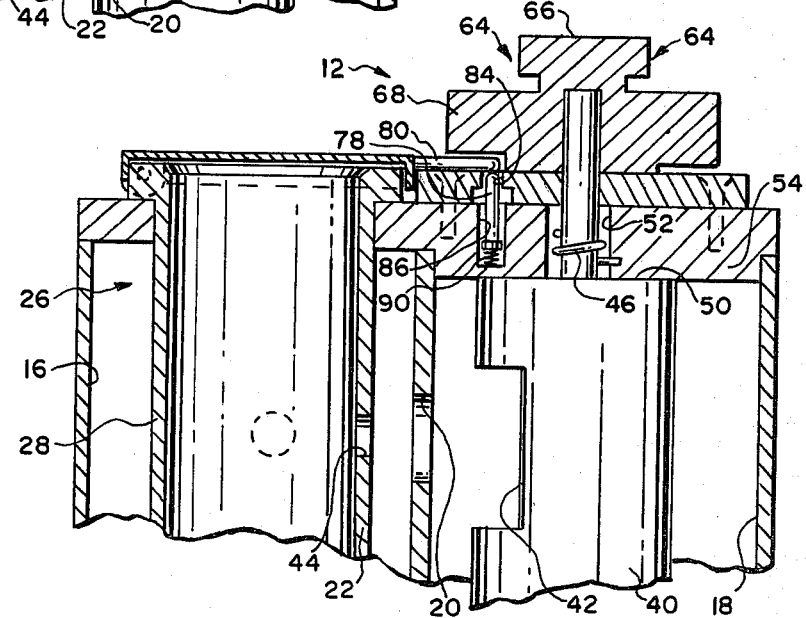
FIG. 5 is a vertical sectional view similar to FIG. 4 showing the cover for the cuvette-receiving chamber in a fully lowered, closed position.
Figure 6:
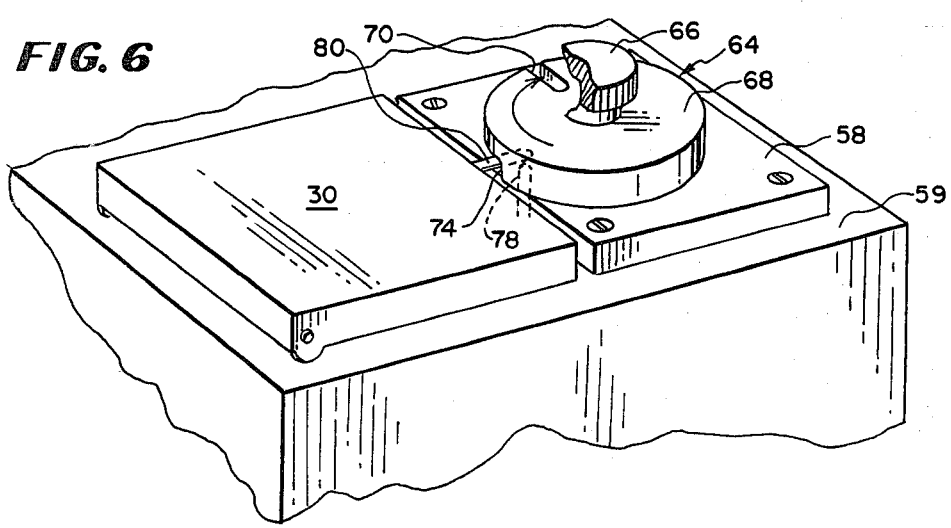
FIG. 6 is a fragmentary perspective view, with portions broken away of the back upper portion of the photometer.

Hidden from view within the photometer 10 shown in FIG. 1 is a light source 14 shown in phantom in FIGS. 1 and 2. This light source 14 is positioned to direct light into a cuvette-receiving compartment 16 (FIG. 3), where it impinges upon a sample in a cuvette (not shown). The fluorescing light radiation generated by the light radiation impinging upon the sample passes from the cuvette-receiving compartment 16 into a photomultiplier-mounting compartment 18 through an opening 20 in a wall 22 between the compartments 16 and 18 (FIG. 3). As best shown in FIGS. 4 and 5, a photomultiplier 24 is mounted in the photomultiplier-mounting compartment 18 and a cuvette holder 26 having a hollow cylindrical body 28 and a hinged cover 30 is received through an opening 32 in the top of the photometer 12 and into the cuvette-receiving compartment 16.

With the arrangement described above, fluorescing light emanating from the sample, which is irradiated by light from the light source 14, passes through the opening 20 into the photomultiplier-mounting compartment 18 to impinge upon the photomultiplier 24. Such amounts of fluorescing light radiation is very low in intensity. Accordingly, a very sensitive photomultiplier 24 is required for sensing the fluorescing light. Also, since the photomultiplier 24 is very sensitive, it is desirable that such photomultiplier 27 not be exposed to the ambient light in the room where the photometer 10 is used. According to the teachings of the present invention, the photomultiplier 24 is protected by the photomultiplier protector assembly 12.

As best shown in FIGS. 2, 3, 5 and 7, the photomultiplier protector assembly 12 includes a cylindrical light shield 40 which is positioned within the photomultiplier-mounting compartment 18 over the photomultiplier 24. In a first position (FIG. 3), shield 40 is designed to block light coming through the opening 20 from impinging upon the photomultiplier. However, when a cuvette is received within the cuvette holder 26 and the cover 30 is moved from an upper raised position shown in FIG. 3 to a lower closed position shown in FIG. 5, the shield 40 automatically moves to a second position, as shown in FIG. 5, where an opening 42 in the cylindrical shield 40 is in registry with the opening 20 and an opening 44 in the holder cylindrical body 28 so that light emanating from the chemical sample in the cuvette can pass through the holder body 28, the wall 22 between the compartments 16 and 18 through the opening 42 in the shield 40 to reach the photomultiplier 24.

The photomultiplier protector assembly 12 is constructed and arranged to provide a mechanical interlock when the shield 40 is moved between the first position blocking the opening 20 and the second position where the opening 42 in the shield 40 is in registry with the opening 20. As will be described in detail hereinafter, this mechanical interlock prevents rotation of the shield 40 when it is in the first position so that the shield 40 is locked in a light-blocking position while the cover 30 of the holder 28 is opened, or the holder 30 is removed from the compartment 16 so that no ambient light can pass through the opening 20; and the mechanical interlock permits, when the cover 30 is closed, the shield 40 to be automatically moved by a spring 46 to the second position where the opening 42 in the shield 40 permits light to pass from the holder 26 into the photomultiplier-mounting compartment 18.

As best shown in FIGS. 3, 4, 5 and 7, the photomultiplier protector assembly 12 includes not only the shield 40 with the opening 42 therein, but also a shaft 48 which is fixed to and extends from an upper end 50 of the cylinder 40. The shaft 40 is received through an opening 52 in the top wall 54 of the photometer 10 and is then slidably received through a bore 56 in a top plate 58. An upper end 60 of the shaft 48 is then splined with a spline 62 to a knob member 64 having a knob 66 and a larger diameter cylindrical apron 68 beneath the knob 66.

The spring 46 is positioned within the opening 52 and one end thereof is fixed to the shaft 48 and the other end is fixed to the top wall 54 of the photometer 10. With this arrangement, the shield 40 is spring biased to the second position shown in FIG. 5 where the opening 42 in the shield 40 is in registry with the opening 20 in the wall 22.

As best shown in FIG. 7, the cylindrical apron 68 has an undercut section 70 which extends between a first end wall 72 and a second end wall 74. Extending through the apron 68 adjacent the first end wall 72 is a slot 76 which is adapted to receive a pin 78 and an elongate tongue 80 therein as will now be described.

The elongate tongue 80 extends from a side 82 of the cover 30 of the holder 26 and is adapted to be received within and through the slot 76. When the tongue 80 is received through the slot 76, it pushes the pin 78 down and is located in the undercut section 70 which then permits the spring 46 to rotate the shaft 48 to rotate the shield 40 to the second position thereof.

The pin 78 is received in openings 84 and 86 extending through the top plate 58 and the top wall 54 of the photometer 10, respectively. Mounted within the bottom of the opening 86 in the top wall 54 is a spring 90 for biasing the pin 78 upwardly.

With the arrangement just described above, the pin 78, whenever it is aligned with the slot 76, will push upwardly into the slot 76. If the tongue 80 is in the slot 76, the pin 38 will push it up out of the slot 76. Also, it will be appreciated that the pin 78 engaging in the slot 76 will lock the assembly 12 with the shield 40 in the first position thereof. Accordingly, whenever the holder 26 is removed or the cover 30 is raised to an open position, the pin 78 engaging in the slot 76 locks the assembly 12 with the shield 40 in the first position blocking light from coming through the opening 20. Then, when the cover 30 is closed and the tongue 80 passes through the slot 76, it pushes the pin 78 against the spring 90 and moves the tongue 80 beneath the slot 76 and into the undercut section 70 where the spring 46 automatically rotates the shaft 48 until the tongue 80 engages the second end wall 74. The engagement of the tongue 80 with the second end wall 74 at one end of the undercut section 70 defines the second position of the shield 40.

It will be apparent that after a fluorescent radiation measurement is made and it is desired to remove a cuvette from the cuvette-receiving compartment 26, an operator will merely grasp the knob 66 and rotate the apron 68 to bring the slot 76 in the apron 68 in alignment with the tongue 80 and the pin 78, where the pin 78 will automatically push the tongue 80 upwardly out of the slot 76 and lock the apron 68 of the assembly 12 with the shield 40 in the first position thereof.

From the foregoing description, it will be apparent that the photomultiplier protector assembly 12 of the present invention provides a number of advantages, some of which have been described above, and others of which are inherent in the invention. More specifically, the assembly 12 provides a unique mechanical interlock which locks the light shield 40 in a light blocking position whenever the cuvette holder 26 is opened or is removed from the compartment 16. Secondly, the photomultiplier protector assembly 12 provides a second interlock arrangement whereby, when the cover of the holder is completely closed, the photomultiplier protector assembly 12 automatically moves the light shield 40 to the second position thereof where the opening 42 in the shield 40 is in registry with the opening 20 in the wall 22 between the compartments 16 and 18.

Also, from the foregoing description, it will be apparent that obvious modifications and variations can be made to the photomultiplier protector assembly 12 of the present invention without departing from the teachings of the invention. Accordingly, the scope of the invention is only to be limited as necessitated by the accompanying claims.

I claim:

1. In a photometer which is particularly adapted for sensing radiation emitted by a chemical sample held in a cuvette in a first compartment and which includes a highly sensitive photomultiplier in a second compartment adjacent the first compartment for detecting fluorescent radiation emitted by the chemical sample and passing through an opening between the compartments, the improvement comprising: means for protecting the photomultiplier from ambient light, said protecting means including a movable cylindrical light shield movable between a first position blocking the opening and a second position not blocking the opening and means for moving said light shield to said first position to protect said photomultiplier from light entering from the first compartment when the first compartment is opened for insertion or removal of a cuvette, and for moving said light shield to said second position not blocking the opening to permit radiation emitted by said chemical sample to impinge upon the photomultiplier in the second compartment, said light shield being made of opaque material and having a single opening therein which is in registry with the opening between said compartments when said light shield is in said second position so that radiation may pass from the chemical sample to the photomultiplier, said moving means including a shaft fixed at one end to the top of said cylindrical shield and coaxial therewith, an upper end of said shaft extending through the top of the second compartment, a knob fixed to the upper end of said shaft, a larger diameter apron beneath and integral with said knob, said apron being constructed with an undercut section opening onto the bottom of said apron and onto the side periphery of said apron through a predetermined arcuate angle so that said undercut section also is defined between a first end wall and a second end wall arcuately spaced from said first end wall in said apron, said apron further having a radial slot therethrough opening onto a top surface of said apron and into said undercut section adjacent said first end wall, a spring biased pin extending from the top of the second compartment, said slot in said apron being aligned with, and receiving therein, said pin when said shield is in said first position, the engagement of said pin in said slot locking said shield in said first position, and the top of the first compartment having a pivoted cover with an elongate tongue extending laterally from a side edge thereof and being received in said slot when the cover is moved from a cover raised position to a cover lowered position, said tongue then depressing said pin below said apron until said tongue is beneath said undercut section, and means for rotationally biasing said apron in one arcuate direction so that when said tongue is beneath said undercut section, said biasing means can move said apron to move said second wall against said tongue where said shield is locked in said second position and the cover is locked in the lowered position, and opening of said cover being enabled by rotating said knob in the opposite arcuate direction against said biasing means until said tongue is received in said slot.

2. The photometer according to claim 1 wherein said first and second end walls defining said undercut section define an angle between 60° and 120°.

3. The photometer according to claim 2 wherein said angle is 90°.

* * * * *